US006258335B1

(12) United States Patent
Bhattacharya

(10) Patent No.: US 6,258,335 B1
(45) Date of Patent: Jul. 10, 2001

(54) CONVERSION OF CARBON DIOXIDE FROM ICE EXHAUSTS BY FIXATION

(76) Inventor: Sanjoy Kumar Bhattacharya, 24455 Lakeshore Blvd. Apt. No. 1804 E, Euclid, OH (US) 44123

( * ) Notice: Subject to any disclaimer, the term of this patent is extended or adjusted under 35 U.S.C. 154(b) by 0 days.

(21) Appl. No.: 09/396,029

(22) Filed: Sep. 15, 1999

(51) Int. Cl.$^7$ .................................................. C01B 31/20
(52) U.S. Cl. ........................ 423/213.2; 423/212; 423/220
(58) Field of Search ................................ 423/212, 213.2, 423/220

(56) References Cited

U.S. PATENT DOCUMENTS

| | | | |
|---|---|---|---|
| 4,285,916 | * | 8/1981 | Baisden ................................ 423/212 |
| 4,477,419 | * | 10/1984 | Pearce et al. ....................... 423/228 |
| 4,624,839 | * | 11/1986 | Wolcott et al. ...................... 423/228 |
| 5,419,121 | * | 5/1995 | Sung et al. ........................... 423/212 |

* cited by examiner

Primary Examiner—Steven P. Griffin
Assistant Examiner—Christina Ildebrando

(57) ABSTRACT

A device comprised of three modular parts (A, B, C) is described here, which allows fixation of carbon dioxide on an acceptor molecule and recycling of the acceptor. This device allows fixation of carbon dioxide from internal combustion engine (ICE) exhausts. In module A of the device, carbon dioxide from the exhausts is fixed onto a five carbon molecule, Ribulose 1,5-bis-phosphate (RuBP) and simultaneously converted into a soluble three-carbon molecule, 3-Phosphoglyceraldehyde. Module B is comprised of a solar panel and a chamber employing a biocatalyst allowing formation of an organic molecule (ATP) that could be used in subsequent steps. ATP generated in module B and 3-Phosphoglycerate generated in module A is used in module C of the device to regenerate Ribulose 1,5-bisphosphate. RuBP generated in module C is used in the first step of carbon dioxide fixation (in module A). On completion of a fixation cycle, the first acceptor molecule RuBP is regenerated for recycle and fixed carbon dioxide could be recovered as soluble organic molecule. Each module is capable of being used as independent device for that part of the process.

4 Claims, 9 Drawing Sheets

Chromatographic analysis of reaction mixture in module A

Quantitative estimation of conversion of RuBP into 3-PGA

Chromatographic analysis of ATP formation from ADP and Pi in Module B

Quantitative estimation of conversion of ADP into ATP

Quantitative estimation of generation of RuBP

… …

CONVERSION OF CARBON DIOXIDE FROM ICE EXHAUSTS BY FIXATION

BACKGROUND OF THE INVENTION

Carbon dioxide is the major gas emitted in the exhaust of stationary or mobile Internal Combustion Engines (ICEs). Globally, a few million motorized vehicles are produced. Most of these employ ICEs which add up to a few million ICEs each year. The emissions from these ICEs are released into the atmosphere. The increased emission of carbon dioxide in the atmosphere has several undesirable consequences such as global warming (1, 2, 3). Thus the Removal of carbon dioxide at the source level into a non-emission or non-polluting entity would be highly desirable. Attempt to fix carbon dioxide from ICEs (stationary or mobile) and convert in situ has not been made. In situ conversion of carbon dioxide into some soluble product, which could be separated and handled in a localized manner, would enable controlling carbon dioxide emission into atmosphere. The product of carbon dioxide fixation could be a valuable material. It is theoretically possible to regenerate the starting material used for carbon dioxide fixation if a five carbon compound is fixed, theoretically, after five cycles of fixation, it is possible to generate a five carbon compound and release the original five molecules and thus allowing for their recycling in the fixation step. Fixation of carbon dioxide and subsequent regeneration of the first molecule used in the fixation step would enable recyclable fixation, which has not been attempted. The fixation and recycling allows obtaining soluble molecules, which could be handled and not emitted into the atmosphere. The fixation and recyclability provides scope for future research where a fuel molecule could be regenerated using an appropriate intermediate first molecule for fixation and a suitable catalyst. Internal combustion engines utilize fossil fuel which has a limited source. With the increased consumption by a fractional increase in the number of ICEs each year the anticipated consequence is the accelerated exhaustion of fossil fuel reserves (4, 5, 6). Research along these lines may also lead to the possibility of developing a fuel recycling technology.

So far a method, a device or utility has not been developed which would enable the fixation of carbon dioxide in emission gases from ICEs. I provide description of utilization of existing knowledge for carbon dioxide fixation used by green plants. In the green plants, the carbon dioxide is fixed in two phases described as light and dark phases (7, 8, 9). In the dark phase, the carbon dioxide is fixed onto a five carbon organic molecule (Ribulose 1, 5 bisphosphate or RuBP). In the light phase, solar energy is used to generate an organic molecule ATP. The organic molecule, ATP, is subsequently used in the recycling process to generate the five carbon organic molecule, RuBP. In difference to plants, conversion of ATP from ADP and inorganic phosphate in this device is made by using electrochemical energy generated by solar cells.

In the present invention, for the first time, I demonstrate that carbon dioxide from the exhausts of internal combustion engines can be fixed to form a soluble organic three carbon organic molecule (3-Phosphoglycerate). A modular solar device allows the formation of ATP molecule using solar energy effected by a membrane bound biocatalyst. Another modular device utilized three carbon organic molecule and ATP to regenerate the five carbon organic molecule for a fresh round of carbon dioxide fixation.

BRIEF SUMMARY OF THE INVENTION

Two important aspects of $CO_2$ emission are addressed in this invention: firstly, the fixation of $CO_2$ to form a soluble organic compound (acceptor) in which the incoming carbon of $CO_2$ is concatenated. This would enable abatement of polluting $CO_2$ at source. The second aspect is after a round of cycle (say five rounds for a five carbon acceptor compound) the allowance for separating a fixed soluble organic molecule simultaneously releasing the acceptor molecule for a fresh round of fixation (recycling).

A device comprised of three modular parts (A, B, C) is described here, which allows fixation and recycling as narrated above. This device allows the fixation of carbon dioxide from internal combustion engine (ICE) exhausts. In module A of the device, carbon dioxide from the exhausts is fixed onto a five carbon molecule, Ribulose 1,5-bisphosphate (RuBP) and simultaneously converted into a soluble three-carbon molecule, 3-Phosphoglycerate. Module B is comprised of a solar panel and a chamber employing a biocatalyst allowing formation of adenosine triphosphate (ATP) that could be used in subsequent steps. ATP generated in module B and 3-Phosphoglycerate generated in module A is used in module C of the device to regenerate Ribulose 1,5-bisphosphate. RuBP generated in module C is used in the first step of carbon dioxide fixation (in module A). On the completion of a fixation cycle, the first acceptor molecule RuBP is regenerated for recycle and fixed carbon dioxide could be recovered as soluble organic molecule. A portion of the 3-PGA generated in module A, apart from being used for regeneration of RuBP, would be extractable.

DETAILED DESCRIPTION OF THE INVENTION

The carbon dioxide gas that is released from the internal combustion engines could be fixed onto a five carbon acceptor organic molecule (RuBP) soluble in water. The carbon of the carbon dioxide is added onto a terminal carbon of the RuBP forming a concatenated carbon chain. This six carbon intermediate is broken down into two three carbon molecules, where carbon atoms are concatenated. These three carbon molecules are converted into different carbon compounds leading to the regeneration of the initial five carbon acceptor molecule and an abstraction of the fixed carbon in the form of a non-polluting soluble carbon compound. The number of carbons in the abstracted molecule during the regeneration of acceptor molecule should, theoretically, depend upon the number of carbon atoms in the acceptor molecule. The number of molecules, which should be used for one complete abstraction would also depend on the number of carbon atom on the acceptor molecule. For example, with a five carbon acceptor, with five molecules in a cycle, it is theoretically possible to fix five carbons, abstract a five carbon molecule and regenerate five-five carbon acceptor molecules. In practice, allowance have to be given for different degree of completion of different intermittent reactions involved and on the route to regeneration which may require more number of molecules for the completion of a single cycle. However, in actual practice in 15 rounds with a 5 carbon compound 15 carbons can be fixed which could be used to generate and extract five molecules of a three carbon compound. The route to fix carbon dioxide suggested and used here, at the basic chemical/biochemical level is utilized by green plants. However, using the biocatalysts derived from the green plants a device has been made enabling the fixation of carbon dioxide from ICE exhausts. For regeneration of the acceptor molecule, energy is required. In the green plants, light energy is used in their specialized organelles to convert into chemical energy (7, 8, 9). In the device described here, however, a solar panel coupled with an electro-bio-chemical device serves this purpose. This electrochemically driven biocatalytic conversion allows synthesis of ATP, which is used for regenerating the acceptor molecule.

Figure 1:
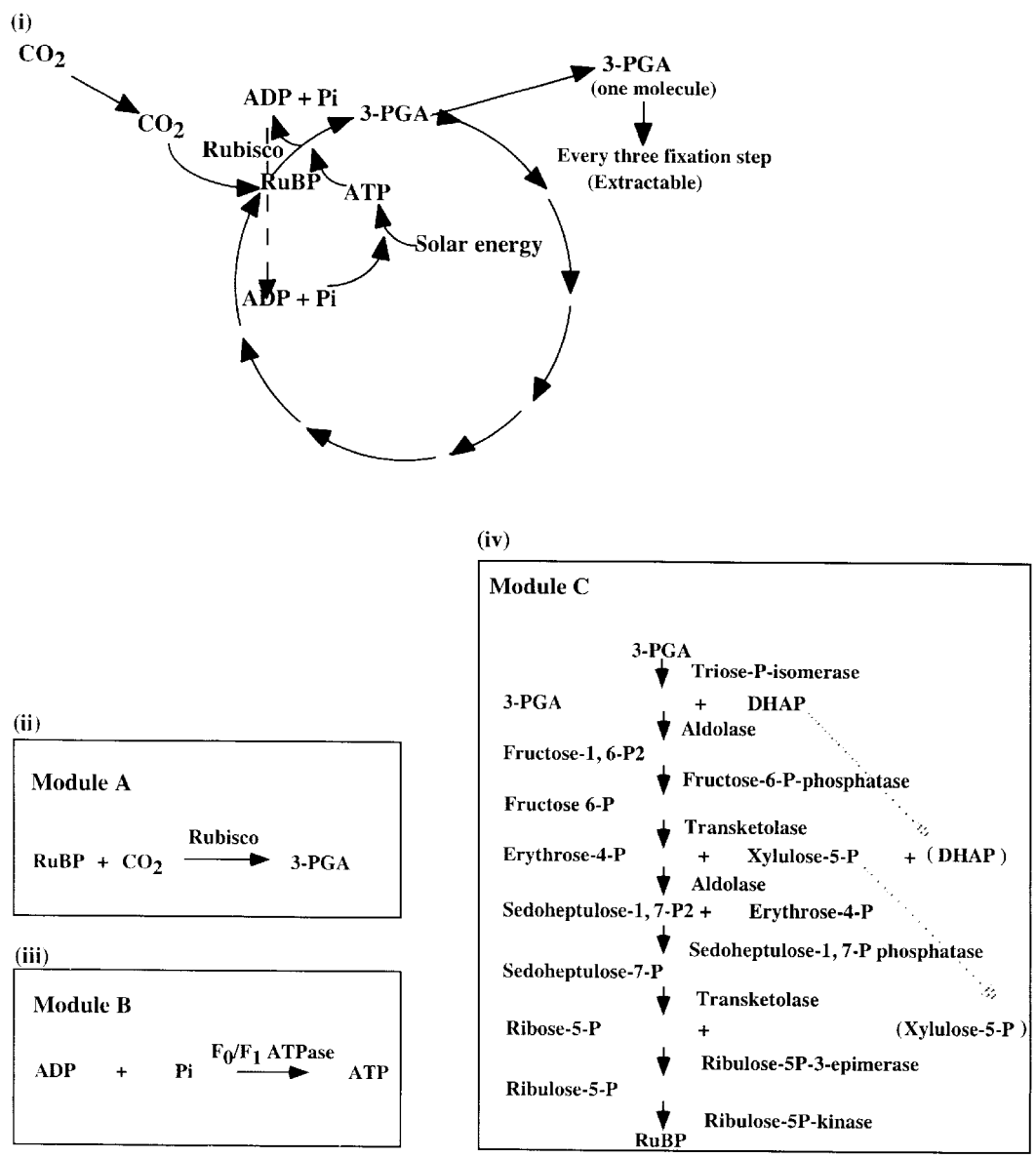
FIG. 1: (i) A schematic representation of the reaction cycle that would enable $CO_2$ fixation and regeneration of RuBP and obtaining extractable 3-PGA. (ii) The schematic representation of the process that occurs in module A. (iii) The schematic representation of the process that occurs in module B. (iv) The schematic representation of the process that occurs in module C. Solid arrows depict forward reactions, the dashed arrows indicate that the reagents, when not converted in the designated reaction are utilized in a subsequent reaction step.

A schematic representation of the process of fixation of carbon dioxide onto an acceptor molecule RuBP and the regeneration of RuBP which is being used for recycling has been presented (FIG. 1). Carbon dioxide from the ICE exhaust (reasonably free from substances that may poison the catalyst) is fixed on to RuBP which is converted into 3-phosphoglycerate and after several inter-conversions, RuBP is regenerated (7, 8). Five cycles of fixation would generate a five carbon moiety, which can be taken away and can be regarded as the net gain from the fixation. That there is a possibility of ATP generation by converting the electrochemical energy into chemical energy using a biocatalyst was first put forth as chemio-osmotic theory (10, 11, 12, 13), which explains the ATP generation in mitochondria and chloroplast. The solar energy in the connected solar panel is converted into electrochemical energy which is used by the enzyme (the biocatalyst, $F_0/F_1$ATPase). This is in accordance with chemio-osmotic theory (10, 11, 12, 13) where a pH gradient or an electrochemical potential gradient enables ATP generation catalyzed by $F_0/F_1$ATPase (12, 13).

Figure 2:
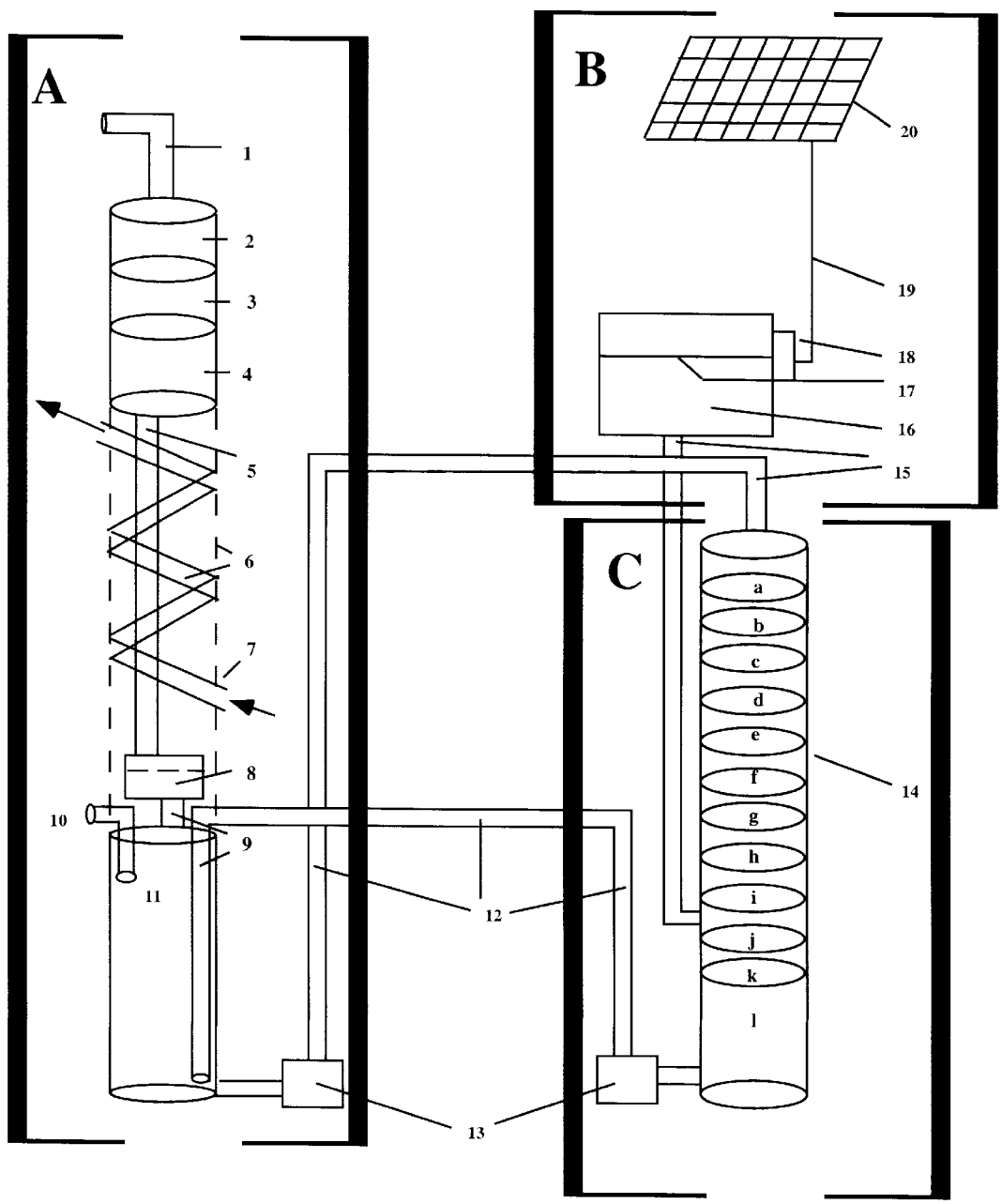
FIG. 2: Sectional view of the device with parenthesis marking the modules. The different parts represented in this diagram are:
1. Connector to the ICE exhaust
2. Catalytic reduction chamber
3. Catalytic oxidation chamber
4. Solid/Liquid $SO_2$ trap
5. Connector tubing for exhaust gas
6. Counter current heat exchanger and its external cover
7. Inlet for Counter current heat exchanger
8. Water reservoir for trapping $SO_2$
9. Connector tubing
10. Safety exhaust
11. Chamber for catalytic conversion by Rubisco
12. Connector tubing
13. Pump
14. A (13+2) chamber conversion device (multiple plug flow reactors): the plug flow type reactors are identified by alphabets and the enzymes they harbor are:
    a. Triose-P-isomerase
    b. Aldolase
    c. Fructose-6-Phosphatase
    d. Transketolase
    e. Aldolase
    f. Sedpheptulose-1,7 P2 phosphatase g. Transketolase
h. Ribulose 5P-3-epimerase
i. Ribose 5P-isomerase
j. Ribulose 5P-kinase
15. Connector tubings
16. ATP generation chamber
17. Semi-permeable membrane
18. Converter and connector panel for electrochemical gradient
19. Connector wire to the solar panel
20. Solar panel with converter

A device is described below, in three modular parts (A, B, C) here which allows the fixation of carbon dioxide from internal combustion engine (ICE) exhausts:

Module (A) FIG. 2.

Figure 3:
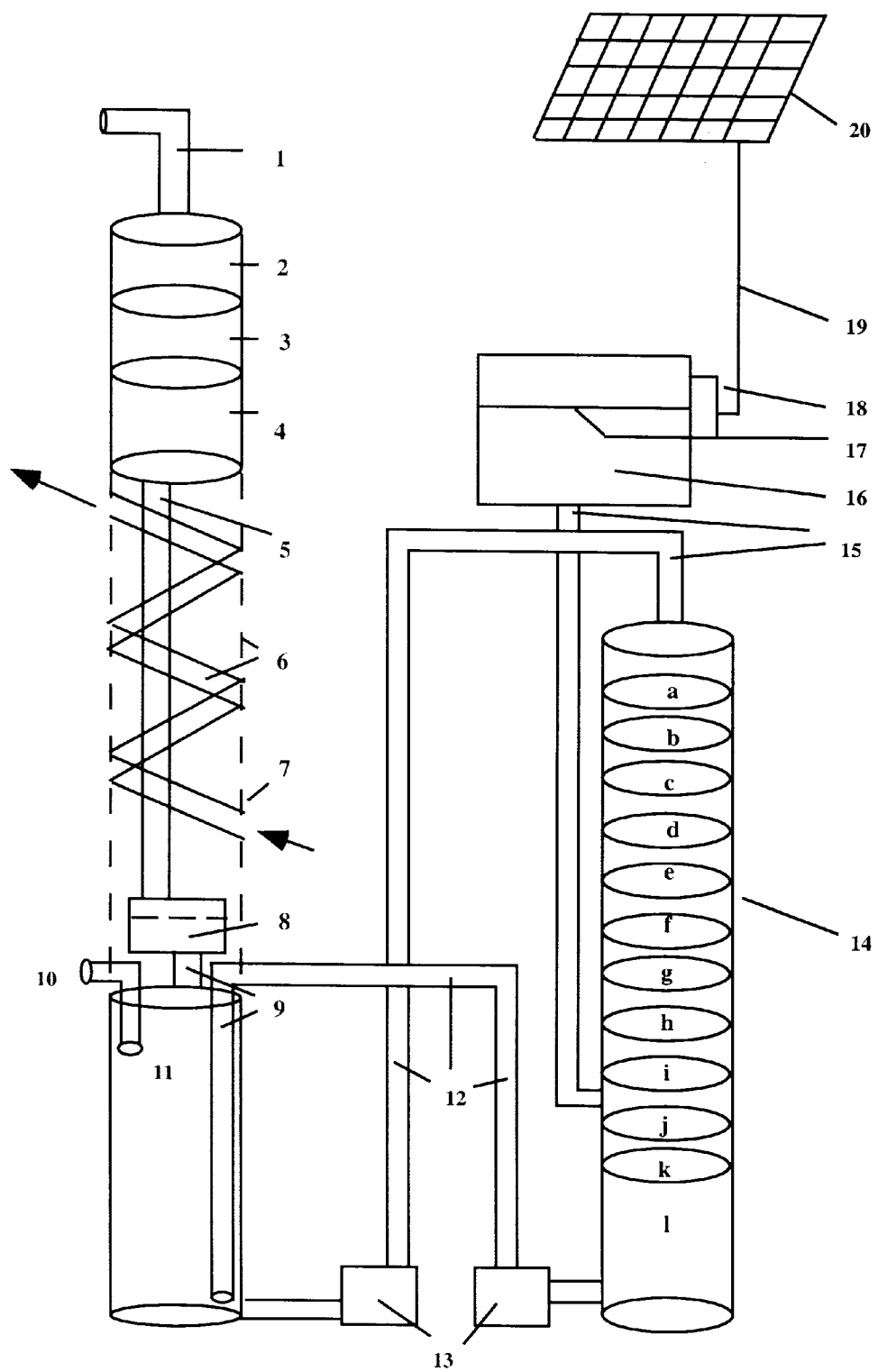
FIG. 3: Sectional view of the device without any marking parenthesis. The parts are identified with identical numbers as in FIG. 2.
Figure 4:
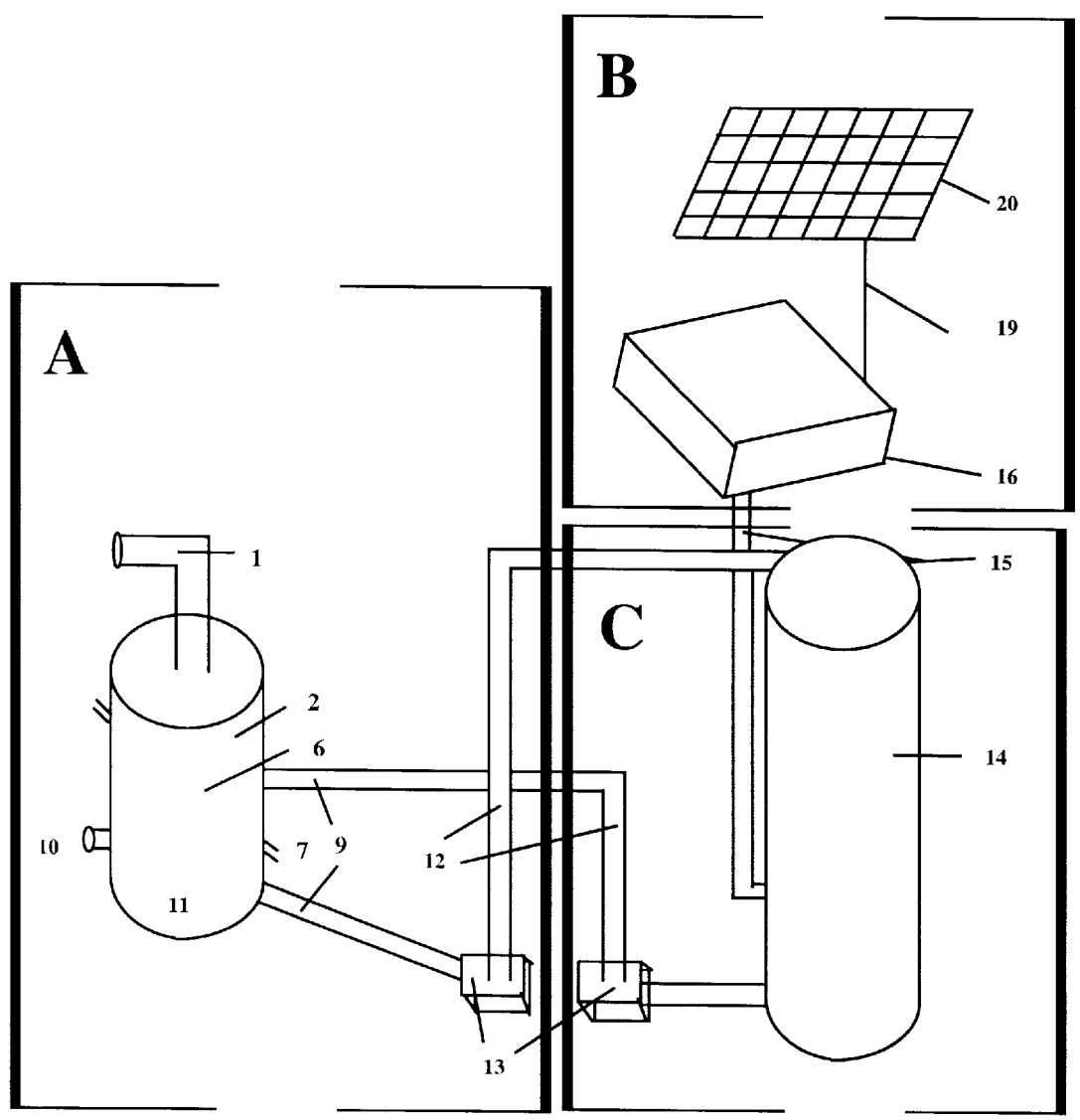
FIG. 4: Exploded View of the device with parenthesis marking the modules. The parts are identified with identical numbers as in FIG. 2.
Figure 5:
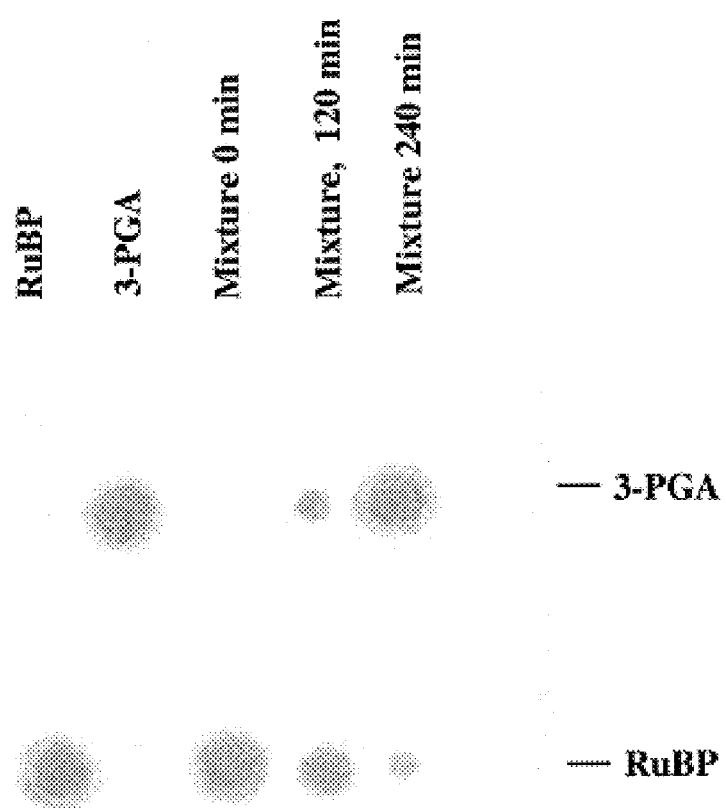
FIG. 5: Chromatographic analysis of conversion of RuBP into 3-PGA. A 20 μl sample from chamber 11 of module A, was spotted onto a Whatman paper number 1 or on a TLC plate run and developed with $AgNO_3$ reagent as described in the experimental procedures. The control RuBP and 3-PGA positions have been indicated. The reaction mixture of module A, chamber 11 was analyzed at different time intervals which has been indicated.
Figure 6:
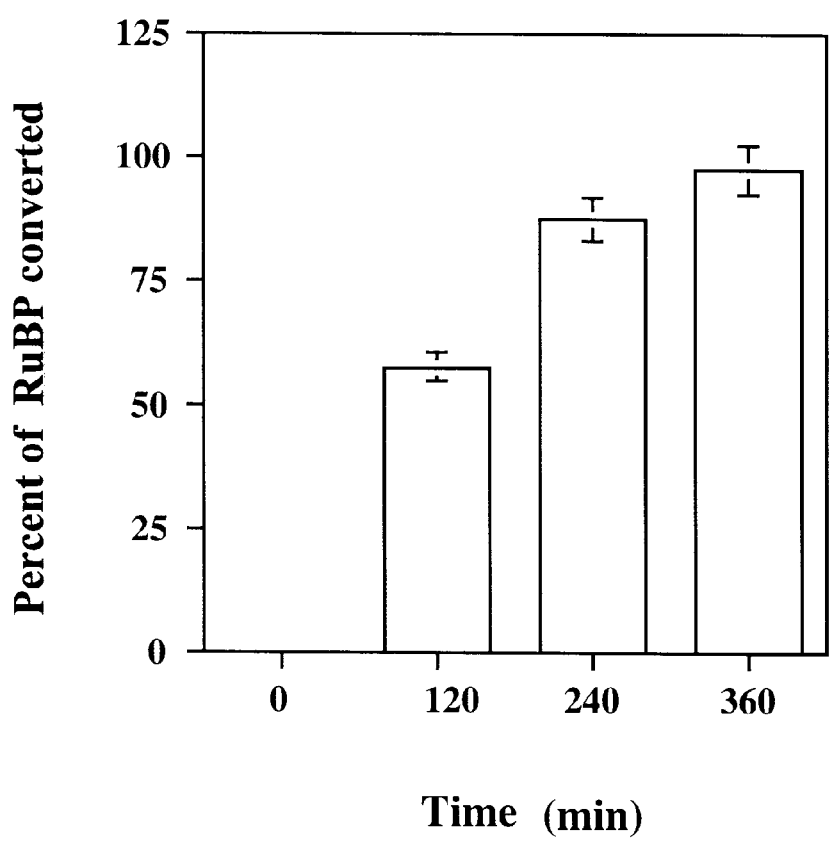
FIG. 6: Quantitative estimation of the conversion of RuBP into 3-PGA based on chromatographic analysis followed by densitometry has been presented. The time period of analysis has been indicated.

In module (A) of the device which is attached to the exhaust of the ICE, the carbon dioxide is fixed onto Rubulose-1, 5-bisphosphate (RuBP) leading to its conversion into a three carbon organic molecule (3-Phosphoglycerate) This reaction is catalyzed by a biocatalyst/enzyme RuBP carboxylase/oxygenase (Rubisco). The design of the module (A) has been schematically represented in the attached FIG. 2. The first part of the module (A) allows the exhausts to be freed of certain gases which renders the biocatalyst irreversibly inactive. This part also allows the cooling of the exhaust emission to prevent the irreversible inactivation of the biocatalyst. In the next part of the module the emission gases are allowed to bubble into a solution where the biocatalyst resides. Before entering in this catalytic chamber, the gas is passed though water in order to eliminate traces of $SO_2$ in the emission gas. This solution in the $CO_2$ fixation chamber also harbors the organic molecule RuBP (five carbon) allowing the carbon dioxide to be fixed and the conversion of the former into a three carbon molecule (3-Phosphoglycerate). The module A as depicted in FIG. 2 has several parts numbered 1–13. The part 1 is the connector to the exhaust, parts 2, 3 house catalytic converters enabling conversion of unwanted gases such as $CO$, $NO_x$, $SO_2$ and unburnt hydrocarbons. In the part 2 of the module, a reducing type catalyst (Rhodium) is kept in a highly porous silica/clay inert support. In part 3, an oxidizing type catalyst (platinum) is kept in a highly porous silica/clay support. In the part 4, $SO_2$ is absorbed in water allowing a reduction in $SO_2$ from the gas emanating from part 4. In part 5, a counter cooling arrangement is made which allows the gas passing from the inner tube to cool down. Part 6 is the housing of the part 5, and the inner tube. Part 7 is the outlet for the counter current exchanger. Part 8 is a water scrubber the turbulence created in the water helps eliminating the particulate matter and allows additional cooling and the elimination of $SO_2$ in the emanating gas. The cooled gas, having a high proportion of $CO_2$, then enters into the chamber 11. Chamber 11 is the reaction chamber having RuBP and the biocatalyst Rubisco maintained under the appropriate condition (14–18). It is magnetically stirred from the bottom. From chamber (part 11), a safety tube (part 10) emanates, which helps controlling excess pressure and is a safety feature of module A. Part 10, or the draft tube remains above the liquid level in chamber 11. The inner tube remains embedded within the liquid level kept inside the chamber 11. Tube 9, which is connected to a pump (part 13), remains embedded in the liquid in chamber 11. FIG. 3 and FIG. 4 are different views of the device. The exhaust gas emissions were obtained by connecting the part 1 of the device with the outlet of a Yamaha EF-1000 Generator having a stationary Internal Combustion Engine (ICE). The chamber temperature (chamber 11) was maintained at 30±5° C. Chamber 11 has a volume capacity of more than 4 liters. The chamber houses Immobilized Rubisco (described under experimental procedures), maintained at a concentration level of 35 mg/Liter. The chamber is filled with a buffer solution having RuBP (about 250 g/liter or ~25% w/v) as described in the experimental procedures. Chromatographic analysis of the solution in chamber 11 with appropriate standards before and after fixation showed conversion of about 98% of the RuBP kept in the fixation chamber (chamber 11) into 3-phosphoglycerate. The fixation was done utilizing the exhaust of 3 liter of petrol from ICE of the Yamaha Generator mentioned above. The chromatographic record (paper and TLC) of conversion of RuBP into 3-Phosphoglycerate, which is the experimental evidence of this specific conversion has been provided in FIG. 5. The quantitative estimations of this conversion have been presented in FIG. 5.

Module B FIG. 2

In the module B of the device which is depicted into FIG. 2, the conversion of an organic molecule ADP and inorganic phosphate into ATP is catalyzed. The conversion is carried out by a biocatalyst ($F_0/F_1$ATPase) at the expense of solar energy. This is achieved by maintaining an electrochemical or pH gradient using solar energy from a solar panel using appropriate converter. The part 16 is the chamber made up of perspex which houses a semi-permeable membrane (part 17) in the middle portion as described in the experimental procedures. The membrane possesses enzyme, $F_0/F_1$ATPase purified from *Steptomycees lactis* (13) immobilized (23, 24, 25) at a concentration level of 1.5–3.0 mg/cm² of the membrane. The upper and lower part of the chamber (part 16) formed as a result of division by the semi-permeable membrane (part 17) is connected with two electrodes from each lower and upper part of the chamber. Part 18 is the connector to the electrodes. The wire (part 19) connects the electrodes (part 18) with the solar panel (part 20), specifications are described under experimental procedures.

Figure 7:
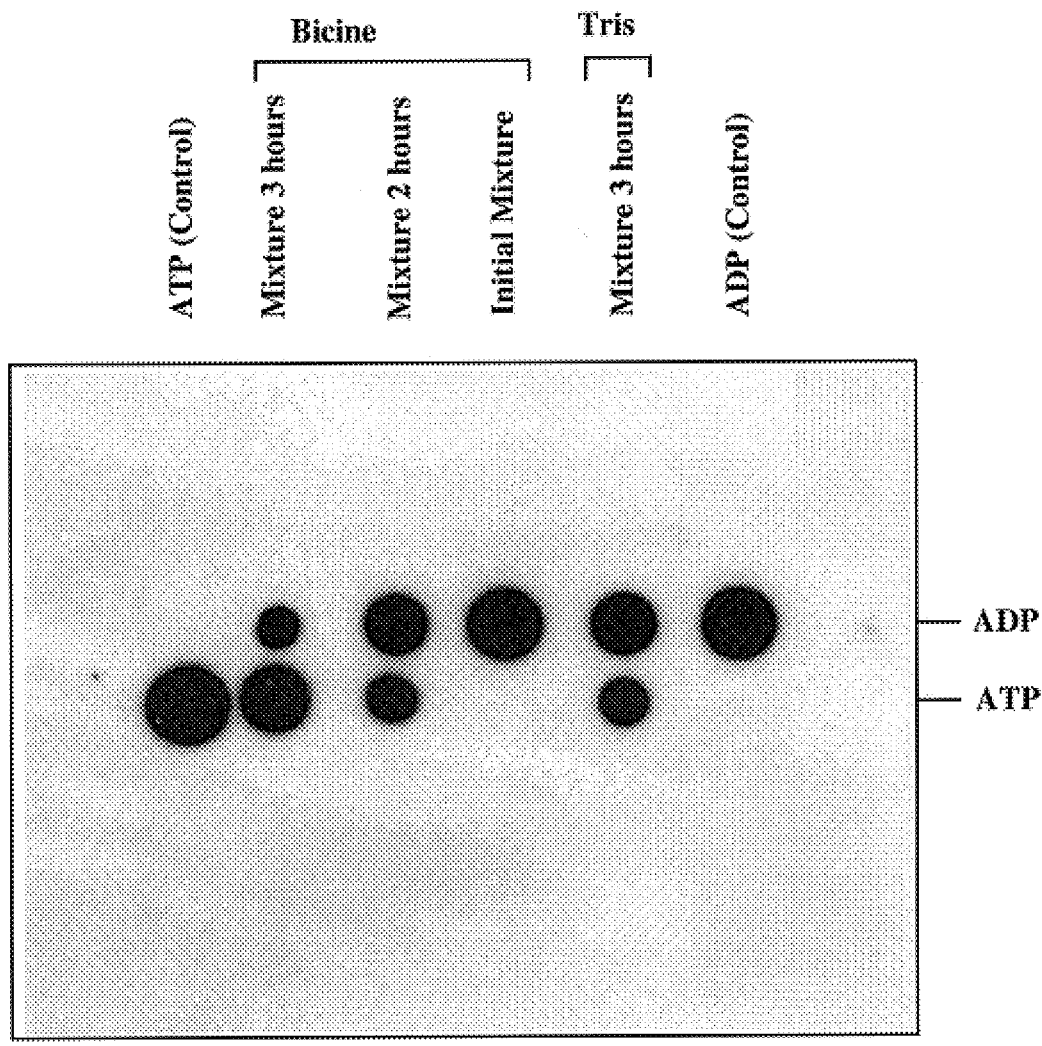
FIG. 7: Chromatographic analysis of conversion of ADP into ATP. This analysis was performed using Radioactivity ADP on a TLC plate as described in the experimental procedures. The positions for radioactive standards ATP and ADP have been identified.
Figure 8:
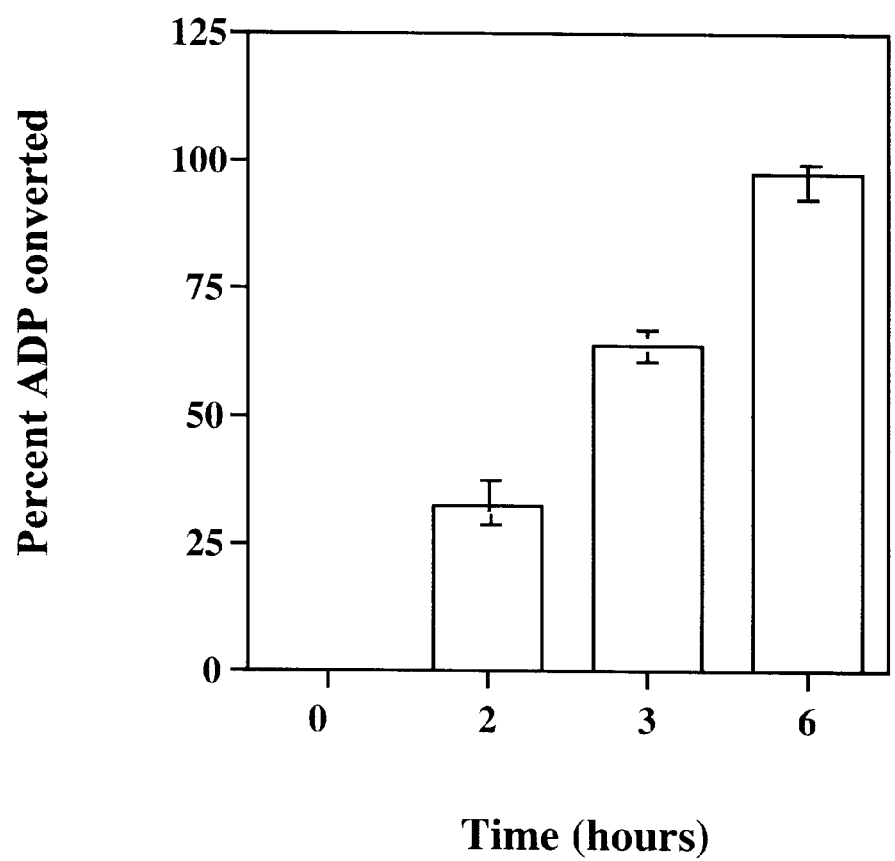
FIG. 8: Quantitative estimation of conversion of ADP into ATP using radioactive analysis and Luminometric assay. A 20 μl sample from chamber 16 of module B was analyzed on a TLC plate. The time intervals at which the analyses were made have been indicated. The solution in chamber 16 was continuously maintained at an electrochemical potential difference of 215 milli volts between the upper and lower chambers.

In the solar panel (part 20), light energy is converted into electrical energy which helps maintaining a negative voltage potential of about 215 millivolts across the membrane. The lower side of the chamber (part 16) is kept at negative voltage. In the inner side of the membrane, a buffer solution (described in methods) is kept at a pH 8.0, while the upper side of the membrane has a buffer having a pH of 7.0. The upper side has ADP and inorganic phosphate buffer at a concentration of 200 mM. Under the influence of an applied electrical potential (215 millivolts) ADP is converted into ATP. Chromatographic analyses revealed >90% conversion of ADP into ATP within a period of 6 hours (FIG. 7). The ATP solution from the lower part of the chamber 16 is fed into part (a) of module C via connector tube 15. The chromatographic analysis of the conversion provided for the experimental evidence. In FIG. 7, chromatographic analyses and in FIG. 8, quantitative estimations have been presented. Confirmations of chromatographic results were also made using a luminometric assay, which has been presented in FIG. 8.

Module C FIG. 2

Figure 9:
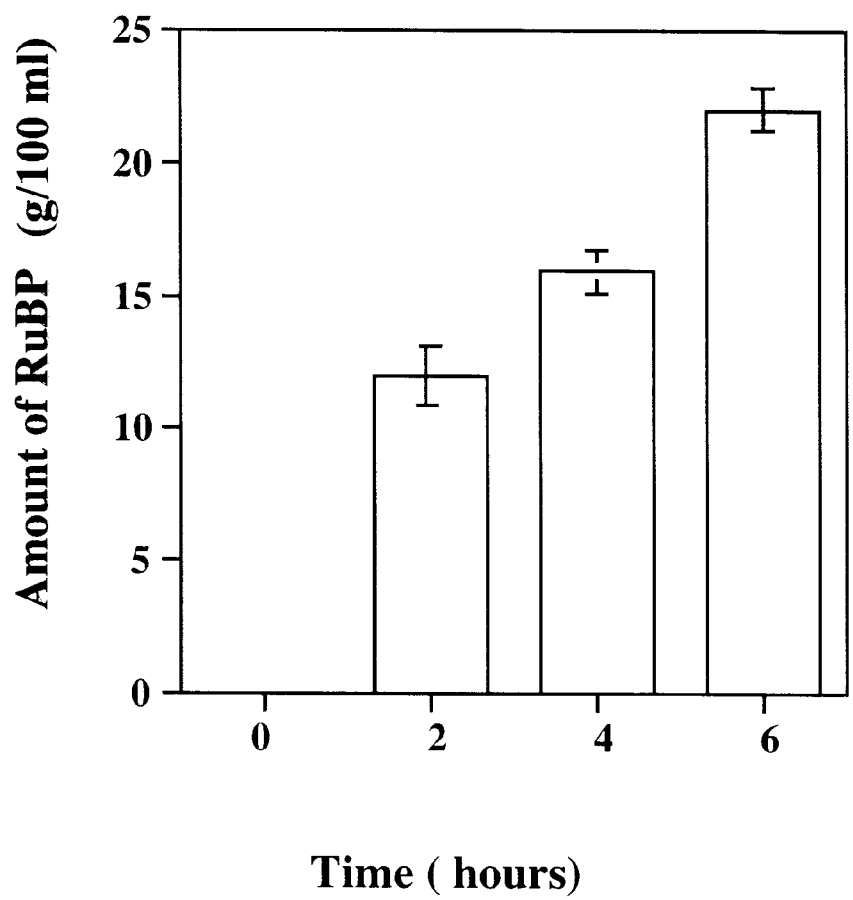
FIG. 9: Quantitative estimation of the conversion of 3-PGA and ATP into RuBP based on determinations as described in the experimental procedures. The time interval at which the analyses were made has been indicated.

The module C of the device has been depicted in FIG. 2. Conversion of 3-Phosphoglycerate (generated in chamber 11) and ATP (produced in module B) are brought to part (a) of module C via connector tube 15. These are to be converted into Ribulose-1,5-bisphosphate as demonstrated using chromatographic analysis. This module comprises a number of immobilized enzymes in appropriate medium in different parts designated as (a) to (l). The reactants 3-Phosphoglycerate and ATP enters into the first immobilized enzyme reactor (part a). Different enzyme reactors are arranged in an array so that the product of the previous reactor acts as the substrate. Chamber (k) is an additional/auxiliary chamber. Chamber (l) is a collector/reservoir chamber from where the solution is pumped. The passage of the aqueous feed is maintained at a slow flow rate of 0.1–0.5 ml/min using a pump so that a uniform residence time distribution is observed in all immobilized enzyme reactors. The ratio of the 3-Phosphoglycerate and ATP to be fed into part (a) has to be in a definite ratio. The chromatographic analysis of the products provided evidence for the presence of Ribulose-1,5-bisphosphate emanating from module C. The quantitative estimation of RuBP generation has been presented in FIG. 9. The RuBP generated in module C is being used in module A in the device. The assemblage of modules (A, B, C), although has been described here, for fixing emission from ICEs but it would work with any emission where carbon dioxide is the major constituent and other gases in emission that may be toxic for Rubisco have been removed. Oxides of nitrogen in the emission stream do not have any adverse effect on Rubisco (or on any other biocatalysts described in these modular devices), therefore no effort is required for the elimination of oxides of nitrogen from the emission gases for carbon dioxide fixation described here.

Experimental Procedures

Module A: $CO_2$ Fixation

ICE Exhaust, the Source of Carbon Dioxide: The Generator:

The internal combustion engine used in these studies was a Yamaha (petrol) Generator, model EF1000. The 84.4cc, 4-stroke, OHV engine generates 1,000 watts maximum AC. This generator may operate up to six or more hours of continuous operation per tank of fuel. It is a brush less generator having a capacitor discharge ignition system.

The Filter Traps: Contaminating Gas Removal Device:

ICE exhausts often contain several gaseous contaminants and particulate matter and the biocatalyst Rubisco may undergo irreversible inactivation in their presence. In addition, the gases emanating from exhaust bear heat which have to be reduced in this device in order to have a suitable $CO_2$ source, having a suitable operating temperature for Rubisco. In order to remove the contaminating gases that are toxic to the biocatalyst, Rubisco, from ICE exhausts to a reasonable extent a filter trap device was fabricated. It has the dimension of 15 cm×75 cm. Module A (FIG. 2) has several parts numbered 1–13. The part 1 is connector to the exhaust, part 2, 3 house the catalytic converters enabling conversion of the unwanted gases such as CO, $NO_x$, $SO_2$ and unburned hydrocarbons. Part 2 and part 3 of module A harbor a reducing type catalyst (Rhodium) and an oxidizing type catalyst (platinum) housed in a highly porous silica/clay inert support. In the part 4, water absorb $SO_2$ in the emission gas, thus allowing its reduction/elimination in the exhaust gas. The purpose of part 1–4 is similar to (which is exhaust gas purification) that of other standard devices available for emission pollution control, such as commercially available Aquacat (AMED Italia, 945 Via Verga, Romanore (Mantova), Italy). Placement of any standard similar device can serve the purpose of this part. The contaminating gases other than carbon dioxide, particularly $SO_2$ has the capacity to poison the biocatalyst for $CO_2$ fixation (nitrogen containing gases for example, $NO_x$ s, has no effect as such), and hence they should be removed before the emission gases could be used as a source of $CO_2$ for fixation by the biocatalyst.

The $CO_2$ Fixation Chamber:

This chamber made up of glass or plastic has a dimension of (12×50 cm.). In a 3 liter volume the final buffer concentrations were 100 mM Na-Bicine buffer (pH 8.2), 10 mM $NaHCO_3$, 20 mM $MgCl_2$, 0.2 mM EDTA and 1 mM dithiotheritol (DTT), enzyme, Ribulose Carboxylase/ Oxygnease (Rubisco) was kept at a concentration of 35 mg/Liter. The buffer was having ribulose 1,5 bisphosphate (RuBP) at a concentration of ~25% (w/v). The connector tube emanating from the filter trap device enters in this chamber. The chamber as shown in FIG. 2 (part 11) has a safety tube (part 10) and is connected to a RuBP regenerator. Safety tube acts as a vent in case of excess pressure build up.

Puririration of Ribulose Carboxylase/Oxygenase (Rubisco):

Rubisco catalyzes the fixation of $CO_2$. Rubisco was purified from Spinach leaves. About 50 g of spinach leaves were washed with 250 ml of Double distilled water in a 500 ml glass beaker. This step was repeated once. Leaf tissues were homogenized in 20 mM Tris-HCl buffer, pH 7.6 containing 10 mM $MgCl_2$, 10 mM $NaHCO_3$, 1 mM EDTA, 5 mM Dithiothretol (DTT) 1%(w/v) polyvinyl pyrrolidone. About 2 ml buffer was used for each gram of tissue. The extract was always kept on ice and centrifuged at 5000 rpm. The clarified supernatant was fractionated with ammonium sulphate, the material precipitating between 35% and 55% saturation was collected and centrifuged. The pellet was dissolved in 20 MM Tris-HCl buffer pH 7.6 containing 1 mM EDTA and 1 mM DTT. The solution was kept in a dialysis bag with a molecular weight cut off of 4000 and dialyzed against 20 mM tris-HCl buffer pH 7.6 containing 1 mM EDTA and 1 mM DTT and 10% glycerol at 4° C. A 50 ml solution was dialyzed against 2×2 liter buffer (14, 15). Rubisco can also be purified from other plants as well as from Synecoccous using the protocols described elsewhere (14, 15, 16, 18).

$^{14}C$ Ribulose-$P_2$ Carboxylase Assay

Rubisco can be assayed by several methods for the estimation of the activity of the purified enzyme (14, 15, 19, 20). One of the most common methods which was used to determine the specific activity of the purified Rubisco is as follows (19):

Reagents: Bicine, 200 mM, pH 8.2, containing 0.4 mM EDTA and 1 mM dithiothreitol, Ribulose-P2, 12.5 mM, pH 6.5.$^{25}$ Store at pH 6.5 in a −20° freezer, $NaH^{14}CO_3$, 250 mM ($\geq 0.14$ Ci/mol), Activated enzyme, 2 mg/ml, $MgCl_2$, 2 M, HCl, 2 N Assay Procedure: These assays are usually run in 8-ml glass scintillation vials to be used for counting the $^{14}C$. Each vial contains 250 μl of Bicine buffer, 20 μl of ribulose-$P_2$ solution, 5 μl of $MgCl_2$ solution, 20 μl of $NaH^{14}CO_3$ solution, and 150 μl of $H_2O$. All reagents except ribulose-$P_2$ and $NaH^{14}CO_3$ are premixed. The vials are stoppered with rubber septum caps to prevent the loss of $^{14}CO_2$ or changes in the specific radioactivity due to exchange with the atmospheric $CO_2$. The stoppered vials may also be gassed with $N_2$. The reaction is initiated after temperature equilibration by the addition of purified enzyme (20 μl) through the rubber septum of the cap. The vial is immediately swirled to mix. (Vigorous mixing with a vortex should be avoided because protein denaturation may occur). After 15 sec to 1 min, the reaction is stopped by the addition of 200 μl of 2 N HCl. The vials, which contain the acidified samples, are slowly heated to dryness in an oven at 95° (in a hood) to remove excess $^{14}CO_2$ and acid. This drying step must be performed carefully to avoid caramelization of the samples, as the color will cause severe quenching during the scintillation counting. After cooling, 0.5 ml of $H_2O$ is added followed by 4.5 ml of scintillation cocktail. The Supertron scintillation cocktail (Kontron) was used.

$$\text{Carboxylase specific activity } (\mu mol/min/mg \text{ protein}) = \frac{^{14}C \text{ (dpm)}}{(\text{dpm } ^{14}C/\mu mol \text{ } CO_2) * \text{time (min)} * \text{mg protein in assay}}$$

When low $CO_2$ concentrations are used, the concentration of enzyme must be correspondingly decreased or carbonic anhydrase added. Otherwise, the $CO_2$ concentration (about 14 μM at 1 mM $HCO_3^-$, pH 8) will change drastically owing to its utilization by the enzyme. Additionally, when various concentrations of $CO_2$ are used in the assay, contaminating $CO_2$ in the buffers can lead to serious and variable errors. It is convenient to determine the specific $^{14}C$ radioactivity of each solution by adding a small amount (about 5 nmol) of ribulose-$P_2$ to an aliquot and converting it quantitatively to [1–$^{14}C$] glycerate-3-P. The observed acid stable radioactivity divided by the amount of ribulose-$P_2$ added gives the specific radioactivity of the $^{14}CO_2$. A separate determination of the total radioactivity in the solution with excess ribulose-$P_2$ can then be used to determine the concentration of $HCO_3^-(CO_2)$. The enzyme is labile in the cold and the enzyme solutions should be handled at room temperature. Ribulose-$P_2$ solutions are unstable, especially under alkaline conditions, and should not be used for more than 2–4 weeks. Ribulose-$P_2$ solutions are stored frozen at a pH of 5–6.5, at which it is most stable, and the assay buffer is relied upon to maintain the pH at 8.2 upon addition of the substrate.

Detection of Sugars and Assay of Rubisco:

Rubisco can be assayed using different methods, radioactive detection method and non-radioactive chromatographic methods (14, 18, 19). The same methods or their appropriate variations can be used for chromatographic analyses of the reactant and products of carbon dioxide fixation on RuBP. The methods, which were actually used in chromatographic analyses, are described in brief below:

Radioactive assay: In radioactive method, radioactive carbon dioxide ($^{14}CO_2$ labeled ) or radiolabeled ribulose 1,5 bisphophate is used for the fixation of $CO_2$. After a fixed period of incubation with the enzyme at 37° C., the solution is subjected to paper or thin layer chromatography. The positions of radioactive spots are noted which are matched with standards for presence of 3-Phosphoglycerate.

Paper chromatography: The substrate ribulose 1,5 bisphophate is incubated in buffer at 37° C. for a fixed period. The aqueous solution is spotted on a chromatographic paper (15×5 cm; Whatman no. 1). All paper-chromatographic separations utilized Whatman no. 1 paper in the solvent system 2-methylpropanoic acid/1 M-$NH_3$/0.1 M-EDTA (125:75:2 by volume). In this solvent system at 23° C., the following relative migration distances, $R_f$ were observed for authentic commercial preparations: ribulose 1,5-bisphosphate, 0.41; 3-phosphoglycerate, 0.72 (20). The chromatographic paper strip should be dipped about 1 cm from the bottom and should hang free. After three hours the chromatographic paper is taken out and air dried. The solvent front is marked with a pencil immediately after taking out the paper. Paper chromatograms were developed by staining with an ammonium molybdate reagent (20% ethanolic solution of 0.5 M ammonium molybdate) to detect sugar phosphate esters or with an $AgNO_3$ reagent to detect total sugars. The spots corresponding to 3-phosphoglecerate is identified using a standard run on the same paper.

Thin layer Chromatograophy (TLC): The substrate ribulose 1,5 bisphophate is incubated in buffer at 37° C. for a fixed period. The aqueous solution is spotted on a TLC plate (2×5 cm; KODAK) and allowed to stand in a glass trough the solvent system 2-methylpropanoic acid/1 M-$NH_3$/0.1 M-EDTA (125:75:2 by volume). The TLC plate was dipped about 1 cm from the bottom and should hang free. After three hours, the TLC plate was taken out and air dried. The solvent front is marked with a pencil immediately after taking out the paper. In this solvent system at 23° C., the following relative migration distances, $R_f$ were observed for authentic commercial preparations: ribulose 1,5-bisphosphate, 0.41; 3-phosphoglycerate, 0.72. The spots corresponding to 3-phosphogleceraldehyde were identified using a standard run on the same TLC plate. TLC plates (like paper chromatograms) were developed by staining with an ammonium molybdate reagent to detect sugar phosphate esters or with an $AgNO_3$ reagent to detect total sugars.

Separation and Identification of Sugars (RuBP and glycerate) by HPLC:

The reaction of Rubisco was carried out in $CO_2$ fixation chamber. Rubisco samples were preincubated in the body of the chamber in a solution containing 100 mM Na-Bicine buffer (pH 8.2), 10 mM $NaHCO_3$, 20 mM $MgCl_2$, 0.2 mM EDTA and 1 mM dithiotheritol (DTT) and Rubisco at a concentration of 35 mg/Liter. The contents of the chamber were allowed to reach at equilibrium for 120 minutes at 25° C. with intermittent stirring with a magnetic stirrer inside the chamber. After 90 minutes of mixing, 100 units of calf intestinal alkaline phosphatase was added and the incubation was continued for another 30 minutes. The contents of the chamber were removed and applied to a 0.5 ml column of BioRad AG1-X8 anion-exchange resin (200–400 mesh, formate form). The column was washed with 10 volumes of milli-Q water and bound radioactivity was eluted with 10% (v/v) $H_2SO_4$. After filtration though a Millipore Ultra-free MC filter unit (10,000 MW nominal cut-off), 0.1 ml of the eluate was chromatographed isocratically on a 0.78×30 cm BioRad Aminex HPX-87H column (organic acid column allows resolution of glycerate, glycolate). The mobile phase was 0.015 N $H_2SO_4$, the flow rate was 0.5 ml/min and the column temperature was 65° C. Absorbance was monitored at 220 nm and 150 ml fractions of eluate were used for scintillation counting (14). [It was necessary to separate ribulose from unreacted RuBP by the alkaline phosphatase treatment before being applied on HPLC column because ribulose co-chromatographed with glycerate. Therefore, dephosphorylated products were first applied to a small column of anion exchange resin which bound the acidic products and allowed any residual ribulose to pass through.]

Entrapment of Rubisco in $CO_2$ Fixation Chamber:

Rubisco from Spinach leaves (15) were immobilized using a PAN-1000 polymer based protocol and used in glass reactors in a batch or continuous mode (19).

The polymer used in the immobilization, PAN-1000, is prepared as described below. A 1-liter round-bottom flask, equipped with a Teflon-coated magnetic stirring bar, is charged with acrylamide (55 g, 0.77 mol), N-acryloxysuccinimide (6 g, 35.6 mmol), azobis (isobutyronitrile) (0.35 g, 2.2 mmol), and 500 ml of tetrahydrofuran (THF) (AR grade, distilled from $CaH_2$). The solution is deoxygenated with argon/nitrogen for 30 min with vigorous stirring. The flask is capped with a Non-Air stopper and maintained in a constant-temperature water bath at 50° for 18–24 hours. During the beginning stages of the reaction, intermittent relief of pressure inside the flask is necessary. The polymer is obtained as a white precipitate at the end of incubation. The precipitated white polymer is separated by filtration on a large Büchner funnel (1-liter capacity). The polymer is washed on the funnel 200-ml portions of dry THF for four times, transferred to a vacuum desiccator, and dried under vacuum (0.02 torr) at room temperature for 18–24 hours. The THF lost during the drying is trapped using a condenser kept at liquid nitrogen temperature to protect the pump. The white product (~60 g), contains about 99% of active ester per gram.

Enzyme immobilization was carried out in the presence of substrates or products intended to occupy the active site and protect it against modification during immobilization. The concentration of substrate Ru-1,5-P (or Ru5-P) used to protect the enzyme was 25–36% (v/v) of a 200 mM solution. A typical example of immobilization procedure of 10–40 mg of enzyme is described below. PAN-1000 (1 g) was placed in a 30-ml beaker containing a stirring bar. HEPES buffer (4 ml, 0.3 M HEPES buffer) containing the active site-protective enzymes was added to it. The mixture was brought into solution within 1 min by vigorous stirring. Aqueous solutions of dithiothreitol (DTT) (50 μl, 0.5 M) and triethylenetetramine (TET, 0.6 ml, 0.5 M) were added; 10 sec later, 1 ml of the enzyme solution in HEPES buffer was added. The mixture gelled within 3 min. The gel was allowed to stand under argon at room temperature for 1 hr to complete the coupling reaction. The gel was ground into fine particles with a pestle in a mortar for 2 min; 25 ml of deoxygenated HEPES buffer [50 mM, pH 7.5, containing 3 mM DTT and 50 mM $(NH_4)_2SO_4$] were added, and grinding was continued for an additional 2 min. The mixture was diluted with the same buffer solution (50 ml), stirred for 15 min to destroy the unreacted active esters, and separated by gentle centrifugation (3000 rpm). The washing procedure was repeated once with the same buffer containing no ammonium salt. The gel particles were then resuspended in the same volume of buffer for reaction/assay.

Module B: ATP Generation

The Solar Cell:

The solar cell (a 12 V, 4.25 Watt solar panel) was obtained from Global Merchants, La Verne, Calif. The panel provides output of varying output of up to 12 Volts and a power equivalent to 4.25 Watt.

Fabrication of the Chamber and Maintenance of pH Gradient:

The chamber consisted of two parts. The upper and the lower chamber parts are boxes each 12 cm×12 cm×12 cm with 2 cm thick walls made up of persplex sheet. Whereas the upper chamber is a hollow box, the lower chamber has a bottom end. Each box has a stoppered drainage system and an electrode port to be connected with an electrode at the external side of the chamber. In the middle position, the member can be adjusted. The lower portion of the chamber has a trough like end on its upper wall where the ridged portion of the upper chamber (lower end) fits. The chambers have clamps on each of their four walls. Once the membrane is placed the upper and lower chamber is closed tightly with solutions contained within them. The membrane is placed in this assembly in such a manner that enzyme bearing side is placed in the lower chamber. In the upper chamber, buffer C (20 mM Hepes, pH 7.0 or 20 mM Tris-HCl pH 7.0) is placed while in the lower chamber buffer D (20 mM Hepes, pH 8.0 or 20 mM Tris-HCl pH 8.0) is placed.

Purification and Preparation of $F_0/F_1$ATPase:

Preparation of enzyme: *Streptoccocus lactis* (ATCC 7962) cells were grown, using a complex media: Bacto-Yeast Extract (Difco), 10 g; Bacto-Tryptone, 10 g; Bacto-Gelatin, 2.5 g; potassium chloride, 4 g; sodium acetate, 1.5 g; ascorbic acid, 0.5 g; and distilled water to a final volume of 1 liter. The pH was adjusted to pH 7 using sodium hydroxide. D-Galactose was added to a final concentration of 1% (13). For experiments, 1 liter medium was inoculated with 10 ml of an overnight grown culture. The culture was incubated at 37° C. without shaking and after about 16–18 hours of growth, the cells were harvested by centrifugation at 8,000×g for 15 minutes at 4° C. The cells were washed twice with 100 mM sodium phosphate, pH 6, and finally resuspended as a concentrated stock in about 5 ml of this buffer. About 5 g of bacterial paste was placed in 5 ml, 2 mM ATP, 2 mM EDTA and 0.15 M Sucrose containing 20 mM Hepes buffer pH 7.2 (maintained at 4° C.), sonicated for ten cycles with amplitude of 22$\mu$. The sonication was performed while keeping the bacterial suspension over ice. The sonicated bacterial suspension was subjected to centrifugation at 20,000 rpm for 30 minutes at 4° C. The supernatant was applied onto a column of Sepharose-hexylammonium (1×15 cm). The supernatant was applied on to the column at a flow rate of 0.5 ml/min. The column was washed with 45 ml of 2 mM ATP, 2 mM EDTA and 0.15 M Sucrose containing 20 mM Hepes buffer pH 7.2. The $F_1$ ATPase was eluted from the column using 1.0 M KCl in the buffer (2 mM ATP, 2 mM EDTA and 0.15 M Sucrose containing 20 mM Hepes buffer pH 7.2). Fractions of 3 ml size were collected and $F_1$ ATPase was eluted between third to fifth fraction. The active fractions were pooled and $F_1$ ATPase was precipitated by the gradual addition of an equal volume of saturated $(NH_4)_2SO_4$ (pH 7.2). The precipitated enzyme was maintained as the $(NH_4)_2SO_4$ precipitate at 4° C., until further experimentation, when it was dialyzed against buffer (2 mM ATP, 2 mM EDTA and 0.15 M Sucrose containing 20 mM Hepes buffer pH 7.2) just before use(13, 21, 22). Frequently some precipitate was found to remain after dialysis which was centrifuged and discarded. The supernatant after centrifugation at 10,000 rpm for 10 minutes was used. For purification of $F_0$ ATPase and reconstitution with $F_1$ ATPase, the bacterial pellet was washed twice with 20 mM Hepes buffer pH 7.2. The pellet was treated with lauryl dimethylaminooxide (LDAO) at room temperature. All subsequent steps were performed at 4° C. Prior to treatement with LDAO the pellet was suspended in 150 mM sucrose and 2 mM EDTA, pH 7.2 in which 1 volume of 15 mM LDAO was added. The LDAO treated pellet was centrifuged at 60,000 rpm. The supernatant contained $F_0$ ATPase. Supernatant was dialyzed against 2 mM ATP, 2 mM EDTA and 0.15 M Sucrose containing 20 mM Hepes buffer pH 7.2. The purified and dialyzed $F_0$ and $F_1$ ATPase were mixed together for reconstitution of $F_0/F_1$ ATPase. This preparation of ATPase obtained from 35 liters of cells was used in the actual experiment (21, 22).

Assay of Enzymatic Conversion of ATP:

The enzymatic conversion of ADP and inorganic phosphate into ATP was confirmed by two independent methods, High Performance Liquid Chromatography and by Thin layer chromatography analysis. The ATP formed was also estimated using a luminometric assay (13).

Measurement of ATP by HPLC Analysis:

Separations of ADP and ATP were carried out in a Varian LCS 1000 HPLC, equipped with a zeiss PM2DLC UV/VIS variable-wavelength detector and a Hewlett-Packard 3385A integrator. The column (1.8×300 mm) filled with Beckman M71 cation-exchange resin (particle diameter: 10 $\mu$m) was eluted isocratically with 0.4 mol/l ammonium formate (pH 4.6) at a flow rate of 0.2 ml/min at 27° C. Column effluents were monitored at 340 nm.

Reversed-phase/ion-pair HPLC separations of lower chamber solutions (ADP, ATP) were carried out in a Hewlett-Packard 1084B HPLC, equipped with a UV/VIS variable-wavelength detector and a semi-automatic injection system. The HIBAR RP 18 reverse-phase column (4×250 mm) from Merck was eluted with a flow rate of 1 ml/min at 60° C. oven temperature. A methanol gradient was established as follows: 0–5 min, 90% pump A+10% pump B: 5–40 min, linear increase from 10% to 90% of total flow by pump B: 40 to 45 min, isocratic elution 10% pump A+90% pump B.

The two reservoirs of the HPLC held the following solutions: (A) 0.6 mmol/l TBADHP. (B) 0.6 mmol/l TBADHP, 50 mmol/l ammonium dihydrogen phosphate in water/methanol (70:30, v/v). TBADHP was taken from a stock solution prepared as follows: crystals of TBAH in water after delivery were immediately titrated to pH 4.8 with 2.00 mol/l phosphoric acid and the precise concentration of the TBAH was calculated from the amount of used acid. The titrated solution was then diluted with DDW to 0.6 mol/l TBADHP and frozen at −80° C. in 2.0 ml aliquots. 1 ml of this stock solution was used to prepare 1000 ml of solution A by mixing it with DDW. To prepare solution B, 56.6 g 85% phosphoric acid (50 mmol acid) and 50 ml DDW were mixed and titrated to pH 4.58 with ammonium hydroxide. The solution was then brought up to 700 ml with DDW and mixed with 1 ml of the TBADHP stock solution. Methanol was subsequently added to give 1000 ml. Finally, solutions A and B were sterilized by filtration, filled into sterilized HPLC flasks and heated to 65° C. and 50° C., respectively. Column effluents were monitored at 340 nm using 450 nm as the reference wavelength.

Measurement of ATP by TLC Analysis:

The samples (5 $\mu$l) were loaded onto a thin layer chromatography plate (TLC) (Kodak, 13255 cellulose). The spots were allowed to air dry. The separation of products were done in a medium containing, 132 ml Isobutyric acid: 40 ml water: 4 ml ammonia solution.

The TLC plates or chromatographic papers in the radioactive method were autoradiographed and intensity of the different spots were determined using a phosphorimager (FUJI BAS 2000). $^{32}P$ labeled moieties were phosphorimaged using BAS 2000 plates. The detection of the spots were made under UV light (365 nm)/trans-illuminator without any use of radioactivity.

Measurement of ATPase Activity by Luminometry:

This method is a modified version of protocol published elsewhere (13). ATP from the reaction mix was extracted by placing 0.4 ml of the centrifuged reaction mixture onto 0.1 ml of ice-cooled 3 N perchloric acid. After about 30 min, the extract was neutralized with 0.3 ml of 1 N potassium hydroxide and kept on ice for an additional 30 min. Firefly lantern extract (FLE-50, Sigma Chemical Co.) was prepared according to the manufacturer's directions and then clarified by centrifugation at 12,000×g for 10 min at 4° C. For the assay of ATP, 0.025 ml of the cell extract was mixed with 0.9 ml of 45 mM glycylglycine buffer, pH 7.4, in a glass vial (scintillation vial). Firefly lantern extract (0.025 ml) was carefully pipetted into the center of the plastic cap, and at the zero time the sample and firefly extract were mixed by inversion. The vial was then placed in the well of a liquid scintillation counter which had been set for maximum sensitivity, with the coincidence circuit off. Fifteen seconds after mixing, the sample was counter for 6 sec. With no added ATP, background counts were about 2,000. When 25 pmoles of ATP were added, about 60,000 counts were obtained. Unknowns contained 0–25 pmoles of ATP and over this range there was a linear relationship between counts and ATP.

Semi Permeable Membrane:

Nylon 66 membrane (dimension 15 cm×15 cm) was used in these studies. Polyurethane and poly(ether)sulfone blend (MPS) membranes were also attempted and their performance are comparable to Nylon 66 membrane (23, 24). Some initial attempts were made with a Goat bladder (dimension 15 cm×15 cm). The bladder was treated with 100 units of collagenase (25 units/ml) for 2 hours at 10° C. and washed extensively using Tris-HCl buffer pH 7.0. It was stored in a refrigerator at 4° C. suspended in 20 mM Hepes buffer, pH 7.0.

Immobilization of ATPase:

Semi purified ATPase from *Streptoccocus lactis* (ATCC 7962) as described above was immobilized using the procedure described below (23, 24, 25). The polyamide (Nylon 66) membranes (mean pore sizes from 0.2–1.2 mm) were used. Polyvinylbenzyl lactonoylamide (PVLA) which is commercially available from Seikagaku Co. (Tokyo, Japan) was also used in immobilization. PVLA was dissolved in Hepes buffer (pH 8) to a concentration of 2 mg/ml with sonication. ATPase solution 10 mg/ml was added in equal ratio to the PVLA solution and incubated over membranes for 15 h at 4° C. After this incubation period, PVLA solution (2 mg/ml) was passed through the membrane several times during a period of 6 hours at 4° C. The membrane was washed with Hepes buffer pH 8 three times. To the washed PVLA 0.01 mM $NaIO_4$ solution added in water was incubated for one hour at room temperature (~23° C.) in the dark. The membrane was washed with Hepes buffer pH 8 three times after the removal of the $NaIO_4$ solution. To periodate oxidized PVLA, ATPase solution (50 mg/ml) and 2% (v/v) borane-pyridine complex were added in Hepes buffer pH 8. The mixture was incubated for 18–20 hours at 4° C. ATPase in 20 mM Hepes buffer pH 8 at a concentration of 10 mg/ml was used to fill membrane pores (1.5–3.0 $mg/cm^2$) by passing the solution through the membrane and subsequently immersing the membrane into the protein solution for 4 hours (23). After the reaction period, 1 M glycylglycine was added and the mixture was incubated for 4 hours. After the removal of the liquid, the membrane was washed with Hepes buffer pH 7.2 three times and further incubated with 2% BSA in Hepes buffer for 1 hour at 4° C. The membrane was washed twice with Hepes buffer pH 7.2 (23, 24). The membrane was dried under vacuum ($1\times10^{-4}$ torr) for 1 minute and kept hydrated under controlled vapor pressure for another 10 minutes (23, 24). A modified diazotization method of coupling (26, 27) was also attempted for these membranes and for the semi permeable goat bladder membrane. However, the diazotization method did not result in satisfactory performance by the immobilized enzyme using this method.

Module C: Regeneration of RuBP

RuBP Regenerator:

This is a chamber with dimensions (12 cm×120 cm). It is connected with two recirculators, one from $CO_2$ fixation chamber and another from ATP generator (part 15). The module C is comprised of 11 consecutively placed plug-flow reactors, designated (a) to (k) and a reservoir chamber (l). These plug-flow type reactors contain immobilized enzymes: Triose-P-isomerase (in reaction chamber a), Aldolase (in reaction chamber b), Fructose 6-P phosphatase (in reaction chamber c), transketolase (in reaction chamber d), Aldolase (in reaction chamber e), Sedoheptulose 1, 7 P2-phosphatase (in reaction chamber f), Transketolase (in reaction chamber g), ribulose-5P-3 epimerase (in reaction chamber h), ribose-5P-isomerase (in reaction chamber i), ribulose-5P-kinase (in reaction chamber j). All these enzymes were immobilized (19, 28, 29) using PAN-1000 polymer as described for Rubisco except for phosphatases which were immobilized using a method described below:

Immobilization Methods for Phosphatases in the Module C:

Methods mentioned in published protocols (28, 29) were attempted with some modifications. Acrylamide (AA) was dissolved in a mixture of 2-vinyl-4,4-dimethylazlactone, ethylene dimethylacrylate and porogenic solvent (tetradecanol ordodecanol/oleyl alcohol mixture) at a temperature of 65° C. Azobis-isobutyronitrile (1 wt % with respect to monomers) was added to the mixture as the last component. A 20×1 mm internal diameter poly (ether ether ketone) (PEEK) reactor tube was placed into a glass vial of a size similar to that of the tube, and the polymerization mixture was added to fill the vial which was then sealed. The polymerization was allowed to proceed at 65° C. for 24 hour. The vial was then broken and the tube retrieved. The excess of polymer outside the tube was removed, and the tube was provided with end fittings and then attached to an HPLC chromatographic system (HP 1050). Methanol (20 ml) and water 91 ml) were pumped through the reactor at a flow rate of 0.2 ml/min to remove the porogenic solvents and soluble compounds present in the monolith after the polymerization was completed. The protein was dissolved in 20 mM Hepes buffer pH 7.2 which also contained 0.05 mol/L benzamidine to achieve a protein concentration of 2 mg/ml. This enzyme solution was pumped through the monolithic reactor at flow rate of 0.2 ml/min for 60 min. Then 1 mol/L ethanolamine solution in water was pumped through the monolith for another 6-min to quench the azalactone rings remaining in the monolith. The immobilized enzyme was preserved in 0.05 mol/L benzamidine in 20 mM Hepes buffer buffer (pH 7.2). No change in activity was recorded after 30 days storage at 4° C.

References

1. Victor, D. G. (1998) Stretegies for cutting Carbon. Nature 395: 837–838.
2. Joos, F., Plattner, G.-K., Stocker, T. F., Marchal, O., Schmittner, A. (1999) Global warming and marine carbon cycle feedbacks on future atmoshperic $CO_2$. Science 284: 464–467.
3. Hoffert, M. I. et. al. (1998) Energy implications of future stabilization of atmospheric $CO_2$ content. Nature 395: 881–884.
4. Parson, E. A. and Keith, D. W. (1998) Fossil fuels without $CO_2$ emissions. Science 282: 1053–1054.
5. Toman, M and Darmstadter (1998) Is oil running out? Science. 282: 47–48.
6. Kerr, R. (1998). The next oil crisis looms large-and perhaps close. Science. 281: 1128–1131.
7. Salisbury, by F. B. and Ross, C. W., Plant Physiology, 4th edition October 1991, Wadsworth Pub Co; San Francisco, USA
8. Lehninger A. L. Principles of Biochemistry (second edition), March 1993, W. H. Freeman & Co., San Francisco, USA.
9. Stryer, L. Biochemistry ($4_{th}$ Edition), March 1995, W. H. Freeman & Co., San Francisco, USA.
10. Mitchell, P. and Moyle, J. (1967) Chemiosmotic hypothesis of oxidative phosphorylation. Nature 213: 137–139.
11. Mitchell, P (1966) Chemiosmotic coupling in oxidative and photosynthetic phosphorylation. Biol. Reviews of the Cambridge Phil. Soc. 41: 445–502.
12. Mitchell, P (1974) A chemiosmotic molecular mechanism for proton-translocating adenosine triphosphatases. FEBS Letters. 43: 189–194.
13. Maloney, P. C. and Wilson, T. H. (1975) ATP synthesis driven by a protonmotive force in *Streptococcus lactis*. J. Membrane Biol. 25: 285–310.
14. Kane, H. J., Vill, J., Entsch, B., Paul, K., Morell, M. K. and Andrews, T. J.(1994) An improved method for measuring the $CO_2/O_2$ specificity of Ribulose bisphosphate Carboxylase-Oxygenase. Aust. J. Plant Physiol. 21:449–461.
15. Wang P. Royer M. Houtz R L. (1995) Affinity purification of ribulose-1,5-bisphosphate carboxylase-oxygenase large subunit epsilon N-methyltransferase. Protein Expression & Purification 6: 528–536.
16. Jordan, D. B. and Ogren, W. L. (1981) Species variation in the specificity of ribulose bisphosphate carboxylase/oxygenase. Nature 291(11):513–515.
17. Lundqvist, T. and Schneider, G. (1991) Crystal structure of activated Ribulose-1,5-bisphosphate carboxylase complexed with its substrate, Ribulose-1,5-bisphosphate. J. Biol. Chem. 266: 12604–12611.
18. Read, B. A. and Tabita, F. R. (1994) High substrate specificity factor Ribulose Visphosphate Carboxylase/Oxygenase from eukaryotic marine algae and properties of recombinant cyanobacterial Rubisco containing "algal" residue modifications. Arch. Biochem. Biophys. 312: 210–218.
19. Pierce, J. W., McCurry, S. D., Mulligan, R. M., Tolbert, N. E. (1982) Activation and Assay of Ribulose-1,5-bisphosphate Carboxylase/Oxygenase. Methods Enzymol. (Colowick, S.P. and Kaplan, N.O. eds.) 89: 47–121.
20. Kuehn, G. D. and Hsu, T.-C. (1978) Preparative-Scale Enzymatic Synthesis of D-[$^{14}$C] Ribulose 1,5-bisphosphate. Biochem. J. 175: 909–912.
21. Dreyfus, G., Ccelis H. and Ramirez, J. (1984) Isolation of the mitochondrial F1-F0 adenosine triphosphatase by Sepharose-hexylammonium chromatography: properties and reconstitution in liposomes. Anal. Biochem. 142: 215–220.
22. Gomez-Puyou, M. T. de and Gomez-Puyou , A. (1977) A simple method of purification of a soluble oligomycin-insensitive mitochondrial ATPase. Arch. Biochem. Biophys. 182: 82–86.
23. Yokoi, H. and Belfort, G. (1994) High-rate membrane supported aqueous-phase enzymatic conversion in organic solvent. Bioseparation 4: 213–220.
24. N. Suzuki, Quesenburry, M. S., Wang, J. K., Lee, R. T., Kobayashi, K., Lee Y. C. (1997) Efficient Immobilization of Proteins by Modification of Plate surface with polystyrene Derivatives. Anal. Biochem. 247: 412–416.
25. Ryu, G. H., Han, D. K., Park, S., Kim, M., Kim, Y. H., Min, B. (1995) surface charactristics and properties of lumbrokinase-immobilized polyurethane. J. Biomed. Mater. Res. 29: 403–409.
26. Bhattacharya, S. K. and Dubey, A. K. (1993) Immobilization of restriction endonuclease SphI. Biochem. Appl. Biotechnol.
27. Agarwal, P. K. and Bhattacharya, S. K. (1999) Exploitation of mechanochemistry of restriction endonucleases: Construction of a Multi RE module Biotech. Bioengg. 65: 233–239.
28. Xie, S., Svec, F., and Frechet, J. M. J.(1999) Design of reactive porous polymer supports for high throughput bioreactors: Poly (2-vinyl-4,4-dimethylazlactone-co-acrylamide-co-ethylene dimethyacylate) Monoliths. Biotech. Bioengg. 62: 30–35.
29. Viswanath, S., Wang, J., Bachas, L. G., Butterfield, D. A. and Bhattacharyya (1998) site directed and random immobilization of Subtilisin on functionalized membranes: activity determination in aqueous and organic media. Biotech. Bioengg. 60: 608–616.

What I claim as my invention is:

1. A process for the fixation of carbon dioxide from the exhaust of an internal combustion engine comprising contacting said exhaust gas with Ribulose 1,5-biphosphate thereby converting carbon dioxide present in said exhaust gas into 3-phosphoglyceraldehyde.

2. The process of claim 1, further comprising contacting said 3-phosphoglyceraldehyde with ATP to regenerate Ribulose 1,5-biphosphate.

3. The process of claim 2, further comprising recycling said regenerated Ribulose 1,5-biphosphate for further fixation of carbon dioxide.

4. The process of claim 2, wherein said ATP is produced from ADP and an inorganic phosphate using solar energy and a biocatalyst.

* * * * *